(12) United States Patent
Rosenberg et al.

(10) Patent No.: US 6,669,883 B1
(45) Date of Patent: Dec. 30, 2003

(54) METHOD AND DEVICE FOR PRODUCING DIFFERENT SOLID DOSAGE FORMS

(75) Inventors: Jörg Rosenberg, Ellerstadt (DE); Werner Maier, Schifferstadt (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/869,666

(22) PCT Filed: Jan. 14, 2000

(86) PCT No.: PCT/EP00/00270

§ 371 (c)(1),
(2), (4) Date: Jul. 2, 2001

(87) PCT Pub. No.: WO00/41668

PCT Pub. Date: Jul. 20, 2000

(30) Foreign Application Priority Data

Jan. 15, 1999 (DE) .................................. 199 01 383

(51) Int. Cl.[7] .............................................. B29B 9/10
(52) U.S. Cl. ...................................... 264/141; 425/363
(58) Field of Search ............................... 264/141, 299, 264/300, 310; 425/363

(56) References Cited

U.S. PATENT DOCUMENTS

| | | | |
|---|---|---|---|
| 4,801,460 A | 1/1989 | Goertz et al. | 424/465 |
| 4,880,585 A | 11/1989 | Klimesch et al. | 264/141 |
| 4,957,681 A | 9/1990 | Klimesch et al. | 264/211 |
| 5,073,379 A | 12/1991 | Klimesch et al. | 424/467 |
| 5,135,113 A | 8/1992 | Mayer et al. | 209/539 |
| 5,761,886 A | 6/1998 | Parkhideh | 53/454 |
| 6,132,659 A | 10/2000 | Rosenberg et al. | 264/140 |

FOREIGN PATENT DOCUMENTS

| | | |
|---|---|---|
| CA | 2232353 | 5/1997 |
| WO | WO 96/19962 | 7/1996 |
| WO | WO 97/15290 | 5/1997 |
| WO | WO 97/15291 | 5/1997 |

Primary Examiner—Mary Lynn Theisen
(74) Attorney, Agent, or Firm—Keil & Weinkauf

(57) ABSTRACT

The invention relates to a process and an apparatus for producing solid dosage forms by molding plastic active ingredient-containing mixtures with use of a continuously operating molding tool with two parts which cooperate to mold the plastic mixture, with at least one part having a plurality of depressions to receive and mold the plastic mixture, wherein one part has at least two groups, which differ in volume and/or shape, of depressions. Dosage forms which differ in shape or size are obtained in one step.

7 Claims, 2 Drawing Sheets

Lane 1 2 3 4 5 6 7 8

METHOD AND DEVICE FOR PRODUCING DIFFERENT SOLID DOSAGE FORMS

The present invention relates to a process for producing solid dosage forms by molding a plastic active ingredient-containing mixture with use of a continuously operating molding tool with two parts which cooperate to mold the plastic mixture, with at least one part having a plurality of depressions to receive and mold the plastic mixture.

The production of solid dosage forms, in particular pharmaceutical dosage forms or foodstuffs or food supplements for humans and animals, by calendering an active ingredient-containing melt is disclosed in a number of publications. This process is based on the embedding of an active ingredient in a melt composed of a carrier, e.g. fatty substances or physiologically tolerated polymers. This usually entails an active ingredient-containing melt or an active ingredient-containing plastic mixture being produced in a mixer and/or extruder and then being fed into a molding tool, e.g. a calender with molding rolls. The calender comprises a pair of counter-rotating molding rolls which have on their surface engravings (depressions) which, for example, correspond to the shape of one half of a tablet. The tablet molding takes place in the region of contact of the two rolls by combination of the tablet composition in one depression on one roll with that in the opposite depression on the other roll. It is also conceivable to combine a molding roll with depressions and a smooth roll or a smooth belt to mold such plastic mixtures. The production of tablets by this process is described in general by DE-A-17 66 546 and U.S. Pat. No. 4,880,585; DE-A-44 46 467 describes the production of lenticular tablets and WO-96/19962 the production of divisible tablets. These processes have considerable advantages compared with the conventional production of dosage forms by, for example, tableting powders and granules under pressure. Thus, melt extrusion with subsequent molding by calendering combines a plurality of stages such as metering in, mixing, plasticizing, molding and singulation, in a single continuous process and thus permits a high output, constant quality and extensive freedom in the shaping, makes few demands on the treatment of the precursors and thus makes it possible to produce large numbers of items economically. These advantages are displayed fully only with really large numbers of items, because of the many parameters requiring optimization in so many stages.

There is an observable trend toward diversification in relation to the dosage and the administration form of active ingredients in many subsectors of the drugs market. This diversification is caused inter alia by increasing demands on the uniformity of the active ingredient dose, which is not as a rule ensured by divisible tablets. The provision of a large number of dosages of the same active ingredient is required, for example, when stabilizing patients on particular active ingredients, e.g. for cardiovascular disorders, when different groups of patients have different dose requirements/response times, e.g. adults/children. A large number of dosage forms differing in the dose of active ingredient is also required for active ingredients with a small therapeutic index and for active ingredients with several medical indications. Thus, for example, in the case of the active ingredient acetylsalicylic acid the dose on use in tablets for pain is 500 mg, whereas the same active ingredient is administered in a dose of only 100 mg as platelet aggregation inhibitor. It is also desirable in many cases to be able to offer several embodiments of an active ingredient preparation, e.g. divisible or nondivisible, lenticular or oblong tablets, in order to meet the requirements of different markets or contract manufacture.

The manufacture of such a large number of different dosage forms has to date been possible only by conventional tableting, with the disadvantages which are known. In addition, with conventional tableting it is possible to achieve different dosages only by different tablet formulas for separate manufacture, and the simultaneous production of different dosages/forms in one tableting machine have not previously been disclosed and is imaginable only with great difficulty.

It is an object of the present invention to provide a process and an apparatus which make it possible quickly, efficiently and cost-effectively to produce simultaneously a large number of different dosages and/or shapings of an active ingredient.

The present invention therefore relates to a process for producing solid dosage forms by molding a plastic active ingredient-containing mixture with use of a continuously operating molding tool with two parts which cooperate to mold the plastic mixture, with at least one part having a plurality of depressions to receive and mold the plastic mixture, wherein one part has at least two groups, which differ in volume and/or shape, of depressions.

Figure 1:
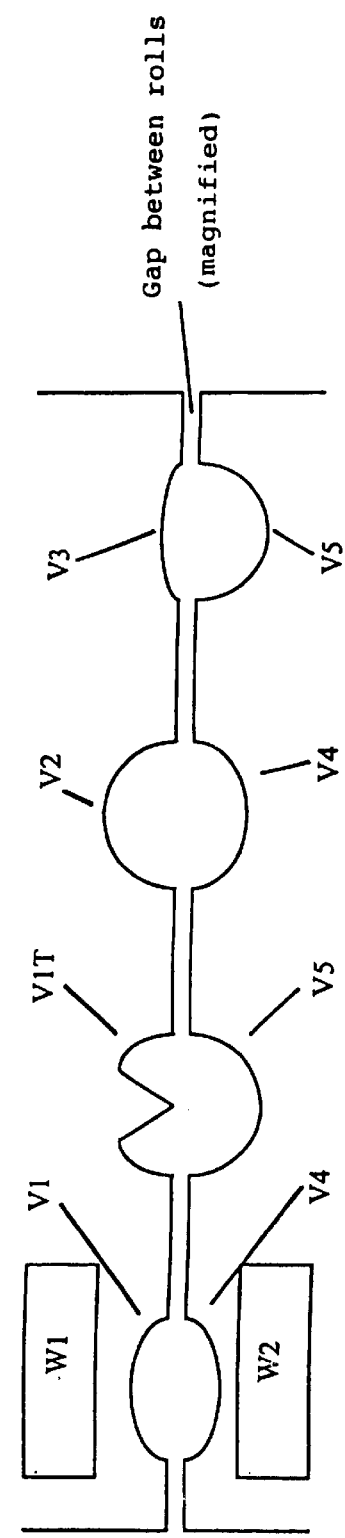
FIG. 1 shows an axial section through a pair of rolls W1 and W2 with different depressions V1, V1T, V2, V3, V4 and V5.

The term "dosage form" herein designates any form for administration of active ingredients to humans, animals or plants. The dosage forms obtained according to the invention are suitable in particular for oral or rectal administration or as implantable active ingredient depots in humans and animals. Particularly preferred dosage forms are tablets of any shape, coated tablets, pellets and suppositories.

It is possible to obtain by the process according to the invention a plurality of different dosage forms in one step. Different dosage forms are dosage forms which differ in volume (and thus in active ingredient dosage) and/or in the shape (e.g. lenticular, elongate, round; divisible, nondivisible etc.).

Whereas in conventional tableting using a tableting machine the density and thus the volume of the tablet depends not only on the mold used but also on the compressive force, in the molding of dosage forms using continuous molding tools such as, for example, calenders with molding belts or rolls which have a defined spacing or are in contact, the volume of the dosage form depends directly on the volume of the depressions in the molding tool. Thus, in this process, the active ingredient content of the dosage form with a given formula (i.e. fixed percentage active ingredient content) depends directly on the volume of the depressions in the molding tools. This is possible because in the process according to the invention there is use of a plastic active ingredient-containing mixture which is preferably essentially incompressible and whose density can therefore, in contrast to the granules and powders employed in conventional tableting, be kept constant within narrow limits. It is therefore possible with the process described herein to produce, by using continuous molding tools with two cooperating parts, at least one of which parts has depressions which differ in volume and/or differ in shape, dosage forms which differ in active ingredient dosage and/or differ in shape from one formula in one step. For this purpose, the molding tool in the process according to the invention is fed with a plastic active ingredient-containing mixture of a composition which is as constant as possible. The different dosage forms are formed or molded solely because of the different groups of depressions in the molding tool.

To produce the plastic mixture it is necessary to mix the constituents, namely at least one thermoplastic, physiologically tolerated, usually polymeric, binder and at least one active ingredient and, where appropriate, conventional additives and convert them into a plastic mixture, preferably in the absence of a solvent. The formation of the plastic mixture can take place by melting or else by kneading, mixing or homogenizing below the melting point of the binder. These process steps can be carried out in a manner known per se, for example as described in EP-A-0 240 904, EP-A-0 337 256, EP-A-0 358 105, WO 97/15290 and WO 97/15291. The contents of these publications are incorporated herein by reference.

The components can be first mixed and then converted into the plastic state and homogenized. However, it has proven preferable, especially when sensitive active ingredients are used, firstly for the polymeric binder, where appropriate together with conventional pharmaceutical additives, to be converted into the plastic state and premixed, operating the apparatuses such as stirred vessels, agitators, solids mixers etc. where appropriate alternately, and then for the sensitive active ingredient(s) to be mixed (homogenized) in intensive mixers in the plastic phase with very short residence times. The active ingredient(s) can be employed in solid form or as solution or dispersion.

The plasticization and mixing take place in an apparatus usual for this purpose. Particularly suitable ones are extruders or heatable containers with agitators, e.g. kneaders (such as of the type mentioned below).

It is also possible to use as mixing apparatus the types employed for mixing in plastics technology. Suitable apparatuses are described, for example, in "Mischen beim Herstellen und Verarbeiten von Kunststoffen", H. Pahl, VDI-Verlag, 1986. Particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (e.g. ORP, CRP, AP, DTB supplied by List or Reactotherm supplied by Krauss-Maffei or Ko-kneader supplied by Buss), trough mixers or internal mixers or rotor/stator systems (e.g. Dispax supplied by IKA).

In the case of sensitive active ingredients, it is preferable first for the polymeric binder to be converted into the plastic state in an extruder and then for the active ingredient to be admixed in a mixer/kneader reactor. On the other hand, with less sensitive active ingredients, a rotor/stator system can be employed for vigorously dispersing the active ingredient.

The mixing apparatus is charged continuously or batchwise, depending on its design, in a conventional way. Powdered components can be introduced in a free feed, e.g. via a weigh feeder. Plastic compositions can be fed in directly from an extruder or via a gear pump, which is particularly advantageous if the viscosities and pressures are high. Liquid media can be metered in by a suitable pump unit.

The mixture obtained by mixing and converting the binder, where appropriate the active ingredient and, where appropriate, the additive(s) into the plastic state is pasty or viscous (plastic) and is therefore extrudable. The binder should preferably be soluble or swellable in a physiological environment. Examples of suitable binders are:

polyvinyllactams, in particular polyvinylpyrrolidone (PVP), copolymers of vinyllactams such as N-vinylpyrrolidone, N-vinylpiperidone and N-vinyl-ε-caprolactam, but especially N-vinylpyrrolidone, with (meth)acrylic acid, (meth)acrylic esters, vinyl esters, especially vinyl acetate, copolymers of vinyl acetate and crotonic acid, partly hydrolyzed polyvinyl acetate, polyvinyl alcohol, poly(hydroxyalkyl acrylates), poly (hydroxyalkyl methacrylates), polyacrylates and polymethacrylates, copolymers of dimethylaminoethyl acrylates and methacrylic esters (e.g. Eudragit types), polyalkylene glycols such as polypropylene glycols and polyethylene glycols (e.g. polyethylene glycol 6000), copolymers of methyl methacrylate and acrylic acid, cellulose esters, cellulose ethers, in particular methylcellulose and ethylcellulose, hydroxyalkylcelluloses, in particular hydroxypropylcellulose or hydroxypropylmethylcellulose, hydroxyalkylalkylcelluloses, in particular hydroxypropylethylcellulose, cellulose phthalates, in particular cellulose acetate phthalate and hydroxypropylmethylcellulose phthalate, and mannans, in particular galactomannans.

It is also possible to use gelatin and biodegradable polymers such as polyhydroxyalkanoates, e.g. polyhydroxybutyric acid, polylactic acid, polyamino acids, e.g. polylysine, polyasparagine, polydioxanes and polypeptides.

Preferred polymeric binders are polyvinylpyrrolidone, copolymers of N-vinylactams, in particular N-vinylpyrrolidone, and vinyl esters, copolymers of N-vinyllactams, in particular N-vinylpyrrolidone, with (meth)acrylic esters, poly(hydroxyalkyl acrylates), poly (hydroxyalkyl methacrylates), polyacrylates, polymethacrylates, alkylcelluloses and hydroxyalkylcelluloses, in particular hydroxypropylcellulose and hydroxypropylmethylcellulose.

Binders which are advantageous for use as plastic binder are those having a K value (method of H. Fikentscher, Cellulose-Chemie 13 (1932), pp. 58–64 and 71–74) in the range between 10 and 100, in particular between 20 and 80.

The polymeric binder must be convertible into a plastic state in the complete mixture of all the components in the range of from 50 to 160° C., preferably 60 to 130° C. The glass transition temperature of the mixture must therefore be below 180° C., preferably below 150° C. If necessary, it is reduced by conventional pharmacologically acceptable plasticizing auxiliaries. The amount of plasticizer does not exceed 30% of the total weight of binder and plasticizer in order to form storage-stable drug forms which show no cold flow. However, the mixture preferably contains no plasticizer.

Examples of such plasticizers are:

long-chain alcohols, ethylene glycol, propylene glycol, glycerol, trimethylolpropane, triethylene glycol, butanediols, pentanols such as pentaerythritol, hexanols, polyethylene glycols, polypropylene glycols, polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol mono-, di- or triacetate or sodium diethyl sulfosuccinate. The concentration of plasticizer is generally from 0.5 to 15, preferably 0.5 to 5, % of the total weight of the mixture.

Conventional pharmaceutical auxiliaries, whose total amount can be up to 100% of the weight of the polymer, are, for example, extenders and bulking agents such as silicates or diatomaceous earth, magnesium oxide, aluminum oxide, titanium oxide, methylcellulose, sodium carboxymethylcellulose, talc, sucrose, lactose, cereal or corn starch, potato flour, polyvinyl alcohol, in particular in a concentration of from 0.02 to 50, preferably 0.20 to 20, % of the total weight of the mixture;

lubricants and release agents such as magnesium, aluminum and calcium stearates, talc and silicones, and animal or vegetable fats, especially in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes may be admixed advantageously alone or together with mono- and/or diglycerides or phosphatides, especially lecithin. The mono- and diglycerides are preferably derived from the abovementioned fatty acid types. The total amount of lubricants and release agents is preferably 0.1 to 5% of the total weight of the composition for each layer;

flow regulators, e.g. Aerosil, in an amount of from 0.1 to 5% of the total weight of the mixture;

dyes, such as azo dyes, organic or inorganic pigments or dyes of natural origin, with preference for inorganic pigments in a concentration of from 0.001 to 10, preferably 0.5 to 3, % of the total weight of the mixture;

stabilizers such as antioxidants, light stabilizers, hydroperoxide destroyers, radical scavengers, stabilizers against microbial attack.

It is also possible to add wetting agents, preservatives, disintegrants, adsorbents and mold release agents (cf., for example, H. Sucker et al., Pharmazeutische Technologie, Thieme-Verlag, Stuttgart 1978).

Auxiliaries include for the purpose of the invention substances for producing a solid solution with the active pharmaceutical ingredient. Examples of these auxiliaries are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, in J. L. Ford, Pharm. Acta Helv. 61, (1986) 69–88.

Pharmaceutical auxiliaries are also regarded as being bases and acids added to control the solubility of an active ingredient (see, for example, K. Thoma et al., Pharm. Ind. 51 (1989), 98–101).

The only preconditions for the suitability of auxiliaries are adequate thermal stability and compatibility with the active ingredient used.

Active ingredients mean for the purpose of the invention all substances with a desired effect, especially pharmaceutical effect, on the human, animal or plant organism and minimal side effects, as long as their decomposition under the processing conditions is negligible. The amount of active ingredient per dose unit and the concentration may vary within wide limits depending on the activity and the release rate. The only condition is that they suffice to achieve the desired effect. Thus, the concentration of active ingredient can be in the range from 0.001 to 95, preferably from 20 to 80, in particular 30 to 70, % by weight. It is also possible to employ combinations of active ingredients. Active ingredients for the purpose of the invention also include vitamins and minerals, and plant treatment agents and insecticides. The vitamins include the vitamins of the A group, the B group, by which are meant besides $B_1$, $B_2$, $B_6$ and $B_{12}$ and nicotinic acid and nicotinamide also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides and vaccines.

The novel process is suitable, for example, for processing the following active ingredients or pharmacologically active salts thereof:

acebutolol, acetylcysteine, acetylsalicylic acid, aciclovir, alfacalcidol, allantoin, allopurinol, alprazolam, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefadroxil, cefalexin, cefazoline, cefixime, cefotaxime, ceftazidime, ceftriaxone, cefuroxime, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, folinic acid, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, imipramine, indomethacin, iohexol, iopamidol, isosorbide dinitrate, isosorbide mononitrate, isotretinoin, itraconazole, ketotifen, ketoconazole, ketoprofen, ketorolac, labetalol, lactulose, lecithin, levocarnitine, levodopa, levoglutamide, levonorgestrel, levothyroxine, lidocaine, lipase, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitaminmixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, pentoxifylline, phenobarbital, phenoxymethylpenicillin, phenylephrine, phenylpropanolamine, phenytoin, piroxicam, polymyxin B, povidone-iodine, pravastatin, prazepam, prazosin, prednisolone, prednisone, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, selegiline, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, zidovudine.

Preferred active ingredients are ibuprofen (as racemate, enantiomer or enriched enantiomer), ketoprofen, flurbiprofen, acetylsalicylic acid, verapamil, paracetamol, nifedipine, captopril, omeprazole, ranitidine, tramadol, ciclosporin, trandolapril and therapeutic peptides.

It is possible specifically for solid solutions to be formed. The term "solid solutions" is familiar to the skilled worker, for example from the literature cited at the outset. In solid solutions of active pharmaceutical ingredients in polymers, the active ingredient is in the form of a molecular dispersion in the polymer.

On extrusion of the plastic mixture it is advantageous to choose the temperature, viscosity and extrusion rate so as to obtain a coherent, self-supporting extrudate. This generally results in continuous production of an extrudate preferably with a constant cross section. It has proven advantageous in many cases to extrude on a downward incline and/or where appropriate to provide a guide channel for transporting the extrudate in order to ensure safe transport and prevent the extrudate being torn off. Depending on the number and compatibility of the active ingredients to be employed, it is also possible and advantageous to employ multilayer extrudates, e.g. coextrudates, as described in WO 96/19963 in the process according to the invention.

The plastic active ingredient-containing mixture described above is fed in the process according to the invention to a continuously operating molding tool. This comprises two parts which cooperate to mold the plastic mixture, at least one of these parts having depressions to receive and mold the plastic mixture. The solid dosage forms are usually produced by feeding the plastic active ingredient-containing mixture into the molding tool in such a way that the plastic mixture is forced into the depressions in the part (or parts) of the molding tool and thus molded to the dosage form.

Depressions mean in this connection recesses or engravings on the surface of the part or parts of the molding tool to receive and mold the plastic active ingredient-containing mixture. The outer margin of the depression on the surface of the particular part is referred to as outline. To make it possible to remove the dosage forms after the molding from the part or parts with depressions, the largest cross section of the depressions is usually on the surface of the particular part, e.g. the outer surface of a molding roll. Downstream of the molding tool there is, where appropriate, also a stripper device, e.g. a stripper roll, stripper brush or the like, which makes possible or facilitates the removal of the dosage forms and/or cleans the molding tool, in particular the parts thereof with depressions.

Particularly suitable molding tools are those having belts and/or molding rolls as cooperating parts, with at least one of the belts and/or at least one of the molding rolls having depressions to receive and mold the plastic mixture. Suitable belts are elastic belts and articulated belts made of polymeric materials, where appropriate with fillers, and/or metallic materials. Belts of these types are usually guided and conveyed by means of guide rolls and/or guide wheels. Suitable belts and belt-containing devices are generally disclosed, for example, in EP-A-0 358 105, the contents of which are hereby incorporated by reference. Belts and/or molding rolls of this these types are preferably disposed in calenders, in which case there is usually combination of at least two belts or two molding rolls or one molding roll with one belt.

It is preferred to use as one part of the molding tool a molding roll which has depressions and is preferably disposed in a calender. It can be combined with a smooth second part, e.g. with a smooth belt, a smooth roll or a smooth wall. This results in dosage forms which are flat on one side and have the shape of the depression on the other side.

The molding tools preferably used for the process according to the invention comprise two cooperating parts having depressions.

Thus, in a particularly suitable embodiment of the process according to the invention, a molding roll having depressions is likewise employed as the other part of the molding tool, with the molding rolls rotating in opposite directions and the outlines of the depressions in one molding roll essentially coinciding pairwise with the outlines of the depressions in the other molding roll in the gap between the molding rolls.

The gap referred to here is the region in which the two parts of the molding tool come closest together, irrespective of whether the surfaces (e.g. outer surfaces) of the parts make contact or are spaced apart.

Counter-rotating molding rolls of this type are preferably disposed in a calender. The plastic mixture can be introduced, for example, by means of a filling wedge into the trough-like space formed between the two molding rolls. The plastic mixture is then taken up and molded by depressions in the counter-rotating molding rolls. The space between the two molding rolls is preferably chosen so that the surfaces of the molding rolls form a small gap, preferably of less than 5 mm and, in particular, of less than 1 mm, or the surfaces of the molding rolls make contact. If it is wished to obtain dosage forms which have minimal projecting burrs or flashes, it is advantageous to adjust the space between the parts of the molding tool, e.g. the molding rolls, to be as small as possible so the resulting gap is as narrow as possible. If it is wished to obtain the dosage forms as coherent strips of dosage forms, it may be advantageous to choose a somewhat larger space between the parts of the molding tool, and thus a far larger gap, or to provide in the peripheral direction between the depressions on the outer surface of the molding roll a connecting channel which is likewise filled with the plastic mixture during molding of the dosage form, and thus connects adjacent dosage forms with connecting flashes or bars to form strips ("string of beads") or ribbons with a plurality of rows of dosage forms connected together.

The depressions of the part (or parts) of the molding tool are to be assigned according to the invention to at least two groups, with the depressions in different groups differing in volume and/or shape. The number of depressions on a part is usually more than 5, in particular more than 10 or more than 50. It is immaterial how many depressions belong to the respective group and how the depressions in a group are disposed on the part.

Different groups of depressions may differ in the shape of the outlines, e.g. into elongate, elliptical or round, in the size of the outlines, e.g. large or small, and/or in the shape of the depressions themselves, e.g. in the volume, in the radii of curvature of the limiting surfaces of the depressions, e.g. shallow lenticular, semicircular, hemispherical and/or by the presence of bars resulting in the formation of scores in the dosage forms and thus in divisible dosage forms.

It is thus possible in one embodiment of the process according to the invention for one part of the molding tool to have a plurality of groups of depressions, in which case, for example, a first group results in the molding of round dosage forms, a second group results in the formation of elongate dosage forms, a third group results in the molding of lenticular dosage forms and a fourth group results in the molding of divisible dosage forms. In another embodiment, one part of the molding tool may have depressions which differ essentially in volume, e.g. small lenticular and large lenticular dosage forms.

On use of two molding rolls it is possible to combine one molding roll W1 with uniform depressions V1 with a second molding roll W2 which has two groups of depressions V1 and V2. This arrangement can be used according to the invention to produce different dosage forms predetermined by the combinations V1 (W1) and V1 (W2) or V1 (W1) and V2 (W2).

On use of a molding roll or of a pair of molding rolls it may be advantageous for the depressions in different groups to be arranged on separate lanes on the molding roll. Lanes mean in this connection in particular an arrangement in which the centers of gravity of the depressions in one group are arranged consecutively in the peripheral direction on the surface of the roll. The individual lanes are, where appropriate, arranged spaced apart in the axial direction.

This arrangement permits removal of the different groups of resulting dosage forms after the molding or after sufficient cooling in separate groups from the molding tool. It is thus possible to obtain the dosage forms sorted into groups in a simple manner. Removal of the dosage forms in separate groups can take place, for example, by separate collection of the dosage forms in each group in separate containers, where appropriate with the aid of separate funnels, deflector plates, suction apparatuses and similar devices for each group, if the dosage forms emerge singly from the depressions or can be removed singly from the depressions, for example with the stripper devices described previously. Removal in separate groups takes place particularly easily if the dosage forms are obtained as strips or ribbons connected by connecting flashes or connecting bars. Singulation of the dosage forms advantageously then takes place in separate groups, e.g. by cutting the ribbons, and they are further processed where appropriate, such as, for example, deflashed and/or rounded off, as described in DE-A-196 29753, the contents of which are incorporated herein by reference. The removal of the different dosage forms in separate groups makes subsequent sorting unnecessary and is particularly advantageous when the dosage forms differ in shape and volume or weight so little that separation by sieving and/or classifying by weight is difficult or impossible.

It is likewise advantageous to arrange the depressions of one group in lanes if, in addition to the plastic mixture, materials in the form of sheets are introduced in each case between melt and molding roll or molding belt, which makes it possible for molding of the plastic mixture to dosage forms to take place at the same time as the coating and/or packaging of the dosage form, as described in WO-96/19963, the contents of which are incorporated herein by reference.

Alternatively, the dosage forms are collected and then sorted into groups. In a preferred embodiment, dosage forms sorted into groups are obtained by sieving and/or classifying by weight the resulting dosage forms. This is particularly suitable when the different dosage forms differ sufficiently in shape and/or volume or weight. It may be necessary, where appropriate, for singulation of the resulting dosage forms to take place only after removal from the molding tool, before sorting by sieving and/or classifying by weight if possible. This is particularly worthwhile when the dosage forms are still wholly or partly connected together on emergence from the molding tool. Processes for sorting dosage forms by sieving and/or classifying by weight are known to the skilled worker.

The resulting different dosage forms can, where appropriate, be further processed, e.g. provided with a coating, together or in separate groups in analogy to known processes in which uniform dosage forms have been obtained.

In a specific embodiment of the process according to the invention there is use of two molding rolls whose depressions are shaped and arranged so that both a first and a second orientation are possible for the molding rolls, it being possible to convert the first orientation into the second orientation by rotation of one of the two molding rolls by 180° relative to at least one axis perpendicular to the long axis of this molding roll. This means that one of the molding rolls can be removed from the molding tool and reinserted so that the original left-hand end is now located on the right; it is then necessary, where appropriate, to resynchronize the rolls. Compatibility of the depressions in the two orientations is ensured, for example, when the outlines of the depressions are disposed to be radially symmetrical relative to at least one point on one rolling of the outer surfaces of each molding roll.

Figure 2:
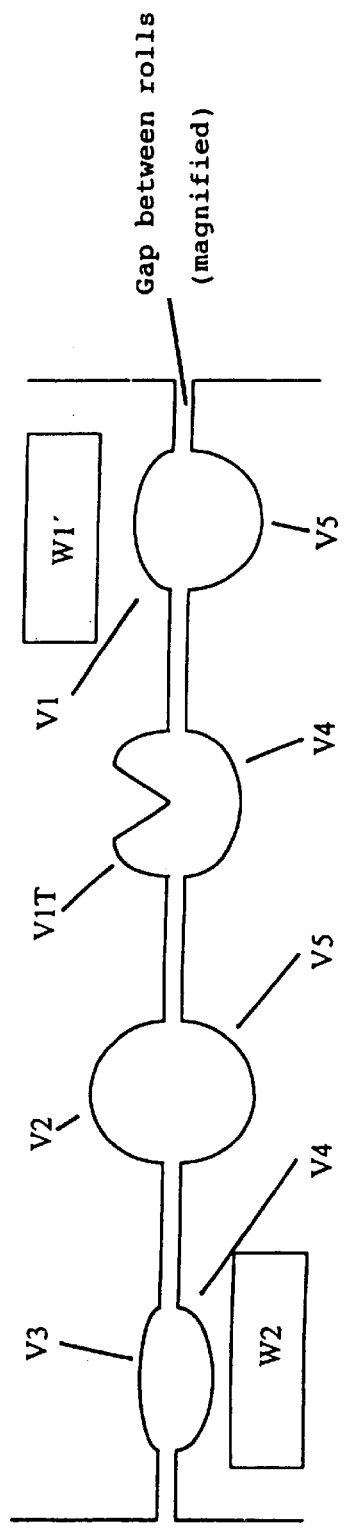
FIG. 2 shows an axial section through a pair of rolls W1' and W2.

The arrangement of the outlines described above is particularly worthwhile when the combinations of depressions in the second orientation differ from those in the first orientation. This can be illustrated by the case shown in FIGS. 1 and 2, where one pair of counter-rotating molding rolls W1 and W2 is used, with molding roll W1 having four lanes of depressions V1, V1T, V2 and V3 and molding roll W2 having alternating lanes V4, V5, V4 and V5. The depressions V1, V2, V3, V4 and V5 differ in shape and volume. V1 and V1T differ by the presence of a bar in V1T, which leads to the formation of a score and thus to a divisible dosage form. All the depressions on W1 and W2 should have the same outlines and be arranged in equal number equidistantly in sequence in the peripheral direction on the particular lane. The spaces between the lanes and the spaces between the outer lanes and the ends of the molding roll are each chosen to be the same. The dosage forms possible with such a combination of molding rolls are depicted in Tables 1 and 2. In this case, W1' represents the molding roll W1 which has been rotated by 180° as described above.

This illustration demonstrates that a large number of different dosage forms can be produced in this way with one apparatus.

TABLE 1

(first orientation)

| W1 | Lane 1 | Lane 2 | Lane 3 | Lane 4 |
|---|---|---|---|---|
|  | V1 | V1T | V2 | V3 |
| W2 | Lane 1 | Lane 2 | Lane 3 | Lane 4 |
|  | V4 | V5 | V4 | V5 |
| Resulting dosage form | V1 + V4 | V1T + V5 | V2 + V4 | V3 + V5 |

TABLE 2

(second orientation)

| W1' (rotated by 180°) | Lane 4 | Lane 3 | Lane 2 | Lane 1 |
|---|---|---|---|---|
|  | V3 | V2 | V1T | V1 |
| W2 | Lane 1 | Lane 2 | Lane 3 | Lane 4 |
|  | V4 | V5 | V4 | V5 |
| Resulting dosage form | V3 + V4 | V2 + V5 | V1T + V4 | V1 + V5 |

The present invention likewise relates to an apparatus for producing various dosage forms by molding a plastic active ingredient-containing mixture, which comprises two parts which cooperate to mold a plastic mixture, with at least one part having a plurality of depressions to receive and mold the plastic mixture, wherein one part has at least two groups of depressions which differ in volume and/or shape. In this connection, the terms "part", "depressions", "plastic mixture" and "groups of depressions" have the meanings described above. The apparatus according to the invention is a continuously operating molding tool. The statements made above in connection with the process according to the invention also apply, unless otherwise evident from the context, to the apparatus according to the invention.

The present invention relates in particular to an apparatus in which one part is a molding roll with depressions. The present invention particularly preferably relates to an apparatus in which the other part is likewise a molding roll having depressions, in which case the outlines of the depressions in the first molding roll and of the depressions in the other molding roll essentially coincide pairwise in the gap between the molding rolls on counter-rotation of the molding rolls. In this connection, the terms "outlines", "gap" and "essentially coincide" have the meaning defined above.

In a specific embodiment, the apparatus according to the invention comprises two counter-rotating molding rolls with depressions, wherein both a first and a second orientation are possible for the molding rolls, it being possible to convert the first orientation into the second orientation by rotating one of the two molding rolls by 180° relative to at least one axis perpendicular to the long axis of this molding roll. In each of the two orientations, the outlines of the depressions on one molding roll and of the depressions on the other molding roll essentially coincide in the gap on counter-rotation of the molding rolls. The axis for the rotation by 180° is fixed by a point on the surface of the roll which is the point of symmetry on rolling the outer surface, and its perpendicular projection onto the long axis of the roll. For the case of least symmetry (single point symmetry), there is only one axis of rotation as defined in the previous description. If there is a plurality of points of symmetry on rolling the outer surfaces of the molding rolls, there is an equal number of axes of rotation given by the perpendicular projection of these points of symmetry onto the long axis of the roll.

In the simplest case, all the depressions have the same outlines, e.g. round outlines, and the arrangement of the depressions on the two molding rolls is mirror-symmetrical relative to a central plane perpendicular to the axis of the roll.

The following example is intended to illustrate the invention without restricting it.

EXAMPLE

Figure 3:
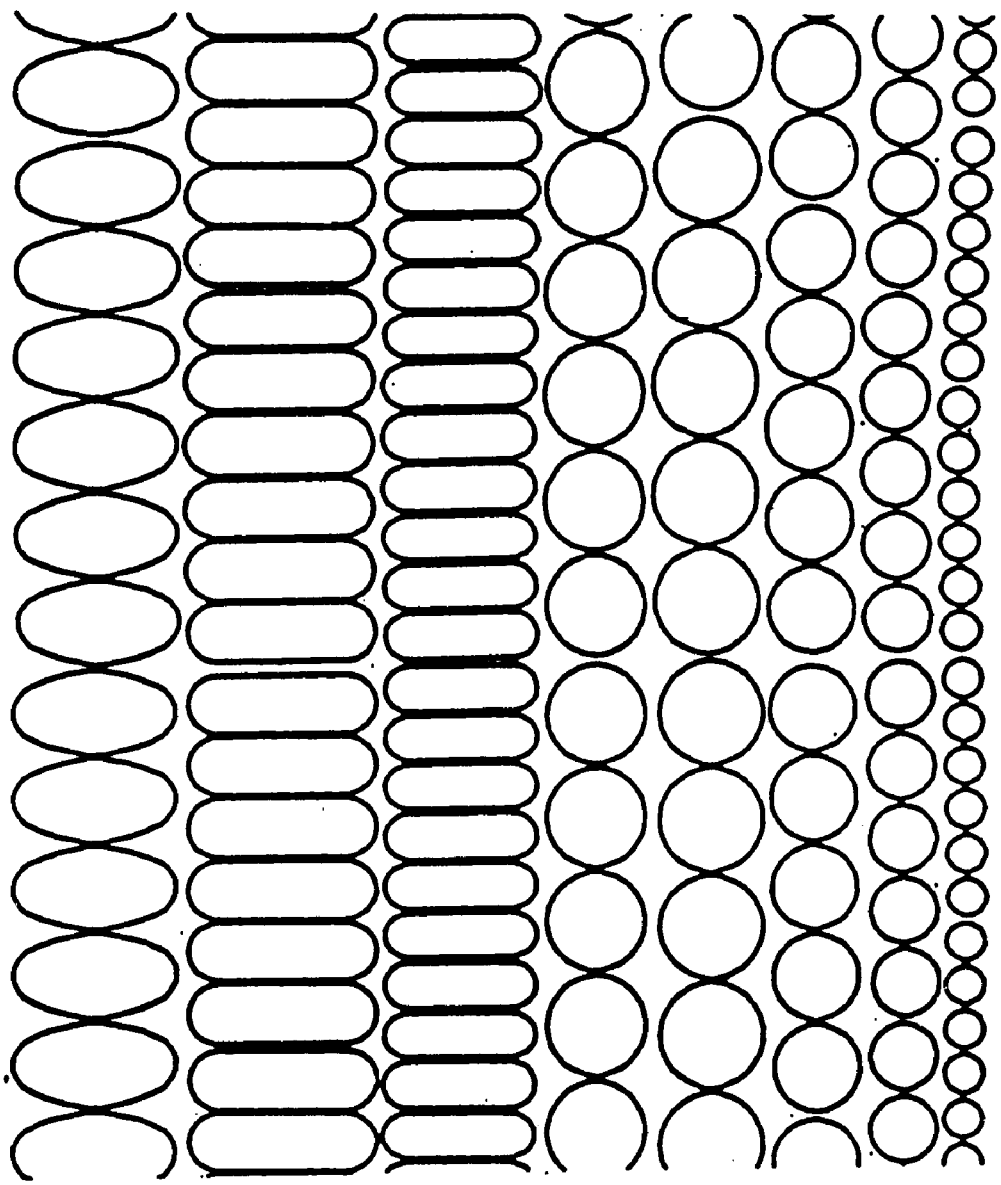
FIG. 3 shows a detail of the rolling from the molding rolls used in the example. The groups of depressions are arranged in lanes 1 to 8.

A plastic active ingredient-containing mixture which contained as active ingredient 48.0% by weight of verapamil hydrochloride and as thermoplastic physiologically tolerated polymeric binder a mixture of 31.5% by weight of hydroxypropylcellulose supplied by Aqualon and 17.5% by weight of hydroxypropylmethylcellulose supplied by Colorcon and as auxiliary 3.0% by weight of lecithin was produced in a co-rotating twin screw extruder (ZSK-40 from Werner & Pfleiderer, Stuttgart), and the active ingredient-containing plastic mixture was extruded at an output of 15 kg/h. The temperature of the plastic mixture was measured shortly before the die and was 120° C. Extrusion took place through a 12 cm-wide slit die. The extrudate was fed into a calender with two counter-rotating molding rolls. Each of the molding rolls had 8 groups of depressions arranged in 8 lanes (lanes 1 to 8), as depicted in FIG. 3. Lanes 1 to 8 are arranged from left to right. The depressions in one group on one molding roll coincide in the gap on rotation with the depressions in the corresponding group on the other molding roll. The outlines of group 1 (lane 1) were elliptical, those of group 2 (lane 2) and group 3 (lane 3) were elongate and those of groups 4 to 8 (lanes 4 to 8) were round. A detail of the rolling of the outer surface of one of the two molding rolls is depicted at the top of FIG. 3.

The different dosage forms produced by calendering were removed as coherent ribbon from the calender and were cooled on a downstream conveyor belt. This was followed by singulation of the dosage forms, and they were separated into groups 1 to 8 by classifying by weight. The weight and the active ingredient content of the different dosage forms produced by the process according to the invention using the apparatus according to the invention are shown in Table 3. The stated weight or the stated active ingredient content of the dosage forms from the different lanes represents the average weight from 100 dosage forms from each group.

TABLE 3

| Molding roll 1 Molding roll 2 | Shape of the outline | Shape of the dosage form | Weight[1] of the dosage form [mg] | Active ingredient content[1] of the dosage form [mg] |
|---|---|---|---|---|
| Lane 1 (group 1) | elliptical | almond-shaped | 408 | 196 |
| Lane 2 (group 2) | elongate | rod-shaped | 656 | 315 |
| Lane 3 (group 3) | elongate | rod-shaped | 325 | 156 |
| Lane 4 (group 4) | round | lenticular | 388 | 186 |
| Lane 5 (group 5) | round | lenticular | 294 | 141 |
| Lane 6 (group 6) | round | lenticular | 160 | 77 |
| Lane 7 (group 7) | round | lenticular | 81 | 39 |
| Lane 8 (group 8) | round | lenticular | 22 | 11 |

[1]average weight from 100 dosage forms from each group

We claim:

1. A process for producing solid dosage forms, comprising i) mixing a thermoplastic, physiologically tolerated polymeric binder which is convertible into a platic state in the range of from 50 to 160° C., at least one active ingredient and, optionally, conventional additives, ii) converting the mixture into a plastic mixture, and iii) feeding the plastic mixture into a molding tool with two parts which cooperate to mold the plastic mixture, with at least one part having a plurality of depressions to receive and mold the plastic mixture, wherein one part has at least two groups, which differ in volume and/or shape, of depressions.

2. A process as claimed in claim 1, wherein a molding roll having depressions is used as one part of the molding tool.

3. A process as claimed in claim 2, wherein a molding roll having depressions is used as the other part of the molding tool, with the molding rolls rotating in opposite directions and the outlines of the depressions in one molding roll essentially coinciding pairwise with the outlines of the depressions in the other molding roll in the gap between the molding rolls.

4. A process as claimed in claim 2, wherein the depressions in different groups are arranged on separate lanes on the molding roll.

5. A process as claimed in claim 4, wherein the resulting dosage forms are removed in separate groups from the molding tool.

6. A process as claimed in claim 1, wherein the resulting dosage forms are sorted into groups by sieving and/or classifying by weight.

7. An apparatus for producing various dosage forms comprising two molding rolls which cooperate to mold a plastic mixture, a) the molding rolls having a plurality of depressions to receive and mold the plastic mixture, b) the molding rolls rotating in opposite directions and the outlines of the depressions in one molding roll essentially coinciding pairwise with the outlines of the depressions in the other molding roll in the gap between the molding rolls, and c) at least one molding roll having at least two groups of depressions which differ in volume and/or shape, wherein the depressions are shaped and arranged on the surfaces of the rolls so that both a first and a second orientation of the molding rolls is possible, it being possible to convert the first orientation into the second orientation by rotating one of the two molding rolls by 180° relative to at least one axis perpendicular to the long axis of this molding roll, and vice versa.

* * * * *